(12) United States Patent
Dong et al.

(10) Patent No.: US 8,557,855 B2
(45) Date of Patent: *Oct. 15, 2013

(54) METHODS OF USING RYANODINE ANTAGONISTS IN TREATING NEURAL INJURY

(75) Inventors: Cun-Jian Dong, Irvine, CA (US); William A. Hare, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 1066 days.

This patent is subject to a terminal disclaimer.

(21) Appl. No.: 10/189,676

(22) Filed: Jul. 3, 2002

(65) Prior Publication Data
US 2004/0006124 A1 Jan. 8, 2004

(51) Int. Cl.
*A01N 43/50* (2006.01)
*A61K 31/415* (2006.01)

(52) U.S. Cl.
USPC .......................................................... 514/392

(58) Field of Classification Search
USPC .......................................... 514/389, 461, 659
See application file for complete search history.

(56) References Cited

U.S. PATENT DOCUMENTS

| | | | |
|---|---|---|---|
| 5,334,618 A * | 8/1994 | Lipton | 514/659 |
| 5,596,011 A * | 1/1997 | Repine et al. | 514/369 |
| 5,891,911 A | 4/1999 | Adorante et al. | |
| 5,922,773 A | 7/1999 | Dreyer et al. | |
| 6,350,780 B1 | 2/2002 | Garst et al. | |
| 6,380,261 B1 | 4/2002 | Dreyer | |
| 6,462,066 B2 * | 10/2002 | Mangat et al. | 514/398 |
| 2001/0053790 A1 * | 12/2001 | Mangat et al. | 514/390 |
| 2004/0006124 A1 | 1/2004 | Dong et al. | |
| 2004/0019118 A1 | 1/2004 | Iqbal et al. | |

FOREIGN PATENT DOCUMENTS

WO WO 90/06118 A1 * 6/1990

OTHER PUBLICATIONS

Anesthesiology, (May 2002) 96 (5) 1053-61.*
E. J. Battegay, "Angiogenesis: mechanistic insights, neovascular diseases, and therapeutic prospects", Journal of Molecular Medicine Jul. 1995 73(7), 333-346.*
Osol A. [Editor] "Chapter 27: Structure-Activity Relationship and Drug Design". Remington's Pharmaceutical Sciences (Sixteenth Edition). Mack Publishing, 1980. pp. 420-435.*
Ambati et al. "Elevated Gamma-Aminobutyric Acid, Glutamate, and Vascular Endothelial Growth Factor Levels in the Vitreous of Patients with Proliferative Diabetic Retinopathy". Archives of Ophthalmology. Sep. 1997; 115(9):1161-1166.*
Greven et al. "Capillary Nonperfusion of the Retina in Diabetes Mellitus". Archives of Ophthalmology. Sep. 1998; 116:1260-1261.*
Luo et al. "Selective Excitotoxic Degeneration of Adult Pig Retinal Ganglion Cells in Vitro". Invest. Ophthalmol. Vis. Sci. 2001; 42:1096-1106.*
Nihard P. "Effect of Calcium-Entry-Blockers on Arterioles, Capillaries, and Venules of the Retina". Angiology. Jan. 1982; 33(1):37-45. [Abstract Only].*
Scott et al. "Improved Retinal Capillary Perfusion Following Treatment of Severe Proliferative Diabetic Retinopathy". Ophthalmic Surgery and Lasers. 2000; 31(2):148-150.*
Stellmach et al. "Prevention of Ischemia-Induced Retinopathy by the Natural Ocular Antiangiogenic Agent Pigment Epithelium-Derived Factor". PNAS, 98(5); 2001:2593-2597.*
Buyukokuroglu et al. "Mechanism of the Beneficial Effects of Dantrolene Sodium on Ethanol-Induced Acute Gastric Mucosal Injury in Rats". Pharmacological Research, 45(5); 2002:421-425.*
"Dantrolene-contg. Therapeutic agent—is useful for treating nerves and brain diseases e.g. Alzheimer's or Parkinson's", Abstract XP002188660.
Frandsen et al, "Dantrolene Prevents Glutamate Cytotoxicity and CA2+ Release from Intracellular Stores in Cultured Cerebral Cortical Neurons", Journal of Neurochemistry, vol. 56, No. 3, Mar. 1991, pp. 1075-1078.
Wei et al, "Dantrolene Inhibits Neuronal Death In Vivo After Cerebral Ischemia and In Vitro After Thapsigargin or Caffeine" Society for Neuroscience Abstracts XP001039860, vol. 21, No. 1-3, 1995, 217.
Lei et al, "Blockade of NMDA Receptor-Mediated Mobilization of Intracellular CA2+ Prevents Neurotoxicity", Brain Research, vol. 598, No. ½;1992, pp. 196-202.
Office Action in U.S. Appl. No. 11/530,537 Date Mailed Mar. 24, 2008.
Office Action in U.S. Appl. No. 11/241,546 Date Mailed Mar. 21, 2008.
Fine et al, "Age-Related Macular Degeneration", Drug Therapy, vol. 342, No. 7, pp. 483-492, 2000.
Barrett et al, "Spontaneous Recovery of Vision in Progressive Anterior Ischemic Optic Neuropathy", Journal of Clinical Neuro-ophthalmology, 12(4), 219-225, 1992.
Lipton, "Ischemic Cell Death in Brain Neurons", Physiological Reviews, vol. 70, No. 4, 1431-1568, 1999.
Moschos et al, "Spontaneous Recovery of Progressive Anterior Ischemic Optic Neuropathy", Metabolic Pediatric and Systemic Ophthalmology, vol. 19&20, 7-11, 1998.
Nowak, "Age-related macular degeneration (AMD): pathogenesis and therapy", Pharmacological Reports, 58, 353-363, 2006.
Stone et al, "Molecular genetics of age-related macular degeneration", Human Molecular Genetics, vol. 10, No. 20, 2285-2292, 2001.
Bains et al, "Neurodegenerative disorders in humans: the role of glutathione in oxidative stress-mediated neuronal death", Brain Research 25, pp. 335-358, (1997).
Lietman, Paul s., et al. "Pharmacology of Dantrolene Sodium in Children," Arch Phys Med Rehabil vol. 55, Aug. 1974, pp. 388-392.
Meyler, W.J., et al., "Relationship Between Plasma Concentration and Effect of Dantrolene Sodium in Man," Eur. J. Clin. Pharmacol. 16, 1979, pp. 203-209.

(Continued)

*Primary Examiner* — Leslie A. Royds Draper
(74) *Attorney, Agent, or Firm* — Krishna G. Banerjee

(57) ABSTRACT

The present invention provides a method of providing neuroprotection to a mammal comprising administering to said mammal suffering from or at risk of suffering a noxious action on its nerve cells an effective amount of a ryanodine antagonist, e.g. dantrolene, to inhibit or prevent nerve cell injury or death.

6 Claims, 1 Drawing Sheet

(56) References Cited

OTHER PUBLICATIONS

Flewellen, E.H., et al., "Dantrolene Dose Response in Awake Man: Implications for Management of Malignant Hyperthermia," Anesthesiology, vol. 59, 1983, pp. 275-280.

Gregory C. Allen, M.D., et al., Plasma Levels of Dantrolene following Oral Administration in Malignant Hyperthermia-susceptible Patients, Anesthesiology, Dec. 1988, pp. 900-904, vol. 69, No. 6.

J. Gen-Nun, et al., Pharmacokinetics of Intravitreal Injection, Assessment of a Gentamicin Model by ocular Dialysis, Investigative Opthalmology & Visual Science, Jun. 1989, pp. 1055-1061, vol. 30., No. 6.

Juan E. Grunwald, Effect of Topical Timolol on the Human Retinal Circulation, Investigative Ophthalmology & Visual Science, Dec. 1986, pp. 1713-1719, vol. 27, No. 9.

Timothy S. Lesar et al., Antimicrobial Drug Delivery to the Eye, Drug Intelligence and Clinical Pharmacy, Sep. 1985, pp. 642-655, vol. 19.

Sujit K. Pandit, M.D., et al., Orally Administered Dantrolene for Prophylaxis of Malignant Hyperthermia, The American Society of Anesthesiologists, Inc., Feb. 1979, pp. 156-158, vol. 50, No. 2.

Kakuji J. Tojo, et al., Pharmacokinetic Model of Intravitreal Drug Injection, Dept. of Biochemical Engineering & Science, Kyushu Institute of Technology, Mathematical Biosciences, 1994, pp. 59-75, Elsevier Science Inc., New York, NY.

Kakuji J. Tojo, et al., Pharmacokinetic model for in vivo/ in vitro correlation of intravitreal drug delivery, ollege of Computer Science and Systems Engineering, Kyushu Institute of Technology, Iizuka Campus, Fukuoka, Japan, Advanced Drug Delivery Reviews, 2001, pp. 17-24, Elsevier Science Inc.

Lavers et al, "Regulation of the calcium release channel from rabbit skeletal muscle by the nucleotides ATP, AMP, IMP and adenosine", J. Physiol. 537: 3, 763-778 (2001).

Paul-Pletzer et al, The Skeletal Muscle Ryanodine Receptor Identified as a Molecular Target of [$^3$H]Azidodantrolene by Photoaffinity Labeling, Biochemistry 2001, 40, 531-542.

\* cited by examiner

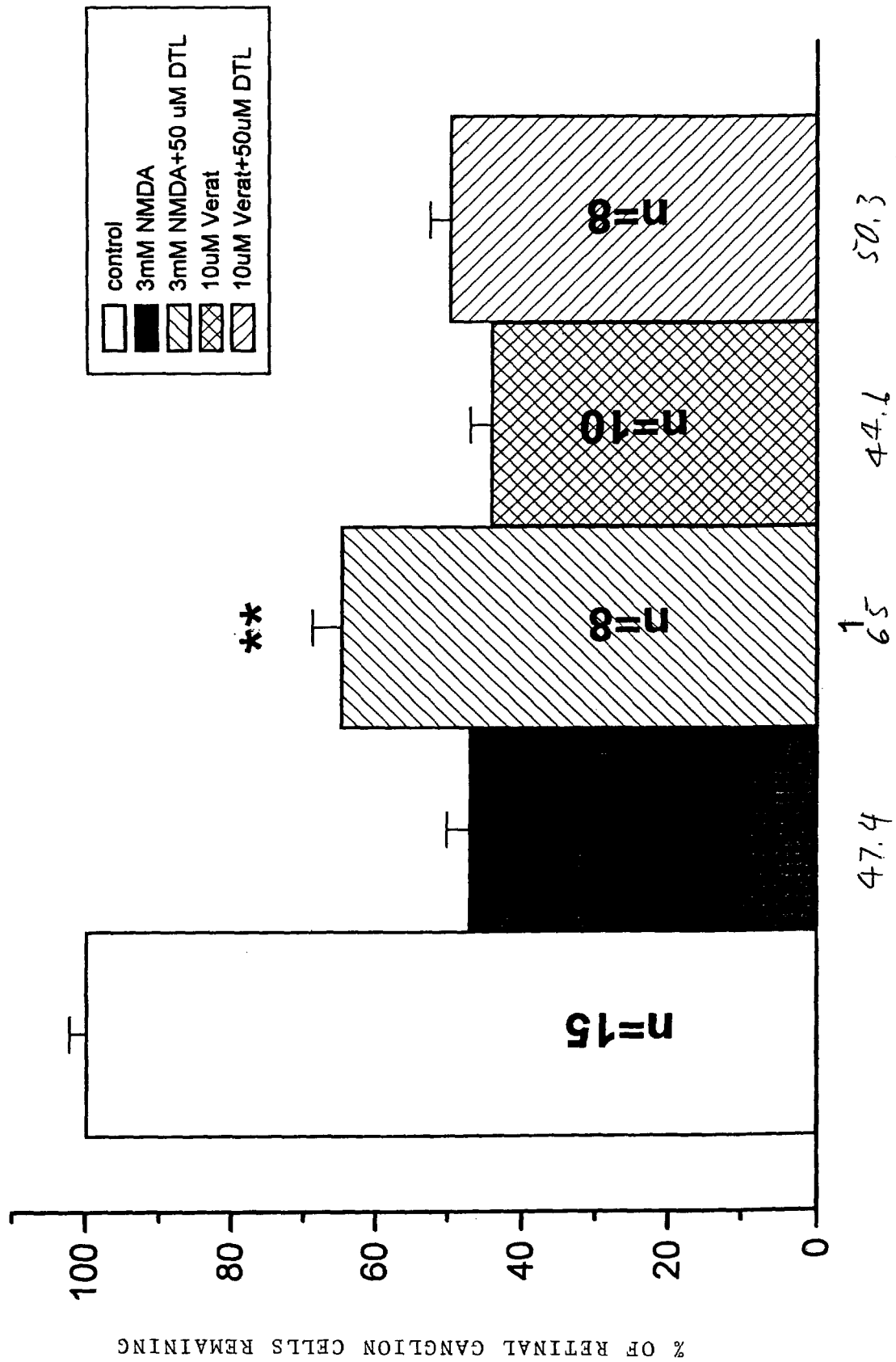

METHODS OF USING RYANODINE ANTAGONISTS IN TREATING NEURAL INJURY

FIELD OF THE INVENTION

The present invention relates to neurology and ophthalmology, and more specifically to protection of neural tissues from injuries caused by abnormal elevation of intracellular free calcium through calcium release from intracellular stores under disease conditions, including stroke, acute brain trauma, Alzheimer's disease, Parkinson's disease, glaucoma, diabetic retinopathy, and age-related macular degeneration.

BACKGROUND OF THE INVENTION

There is compelling evidence that abnormally elevated intracellular free calcium is one of the early events in the chain of reactions leading to neuronal damage under pathological conditions that range from acute neural injuries, such as stroke, to more chronic indications, such as Alzheimer's disease. High intracellular free calcium can cause mitochondrial injury and activate various types of enzymes, such as proteases, nitric oxide synthases and endonucleases. These calcium-induced/activated cellular responses are believed to mediate cytotoxicity that eventually leads to neuronal death.

There are two major mechanisms that can cause elevation of intracellular free calcium: 1) calcium influx from extracellular space through calcium and non-selective cation channels on the cell membrane, and 2) calcium release from intracellular stores, such as endoplasmic reticulum and mitochondria, through specialized receptor-channel complex, such as ryanodine receptor channels. These two mechanisms often interact. For example, calcium entered the cell through ion channels on the cell membrane can trigger more calcium release from intracellular stores. This calcium-induced calcium release (CICR) has been demonstrated to contribute to neuronal damage under pathological conditions.

Glutamate is the major excitatory neurotransmitter in the brain, including the retina. Its biological action is mediated by a variety of glutamate receptors, including the NMDA receptor that is an ionotropic receptor coupled with a non-selective cation channel that has high calcium permeability. Under pathological conditions, glutamate becomes a neurotoxin that causes neuronal damage in both acute neural injuries, such as stroke, to more chronic indications, such as Alzheimer's disease. This glutamate excitotoxicity is mediated, to a large extent, by the NMDA receptor because of its high calcium permeability. Over stimulation of the NMDA receptor resulting from either excessive release or reduced reuptake of glutamate causes intracellular calcium overload that can eventually lead to neuronal death. Calcium entering the neuron through NMDA channels can stimulate more calcium release from intracellular stores via specialized ligand-activated channels, such as ryanodine channels. This calcium-induced calcium release amplifies cellular response triggered by NMDA receptor activation and has been shown to contribute to excitotoxicity under pathological conditions.

Glaucoma is a neurodegenerative retinal disease characterized by progressive death of retinal ganglion cells (RGCs, the output neuron of the retina), which leads to progressive vision loss and eventually to complete blindness. Glaucoma can be classified into two major categories: hypertensive and normotensive. The underlying causes for glaucoma are still not well understood. The initial insults for the two types of glaucoma are likely different. High intraocular pressure is believed to be a major risk factor for the hypertensive glaucoma whereas the vascular abnormality is though to play a significant role in initiation and progression of the normotensive glaucoma. Despite the difference in initial insults, progressive death of RGCs appears to be a common feature shared by both types of glaucoma.

There is increasing evidence that glutamate-induced excitotoxicity plays a significant role in the pathology of glaucoma. It has been demonstrated that glutamate concentration in vitreous humor from the glaucoma patients is significantly higher than that of normal subjects and the vitreal glutamate concentration increases with the years with glaucoma. It has also been shown that the NMDA receptor antagonist, memantine, ameliorates RGC loss in glaucomatous monkeys, suggesting that the NMDA receptor mediates, at least in part, glutamate-induced damage to RGCs in glaucoma.

Diabetic retinopathy is another chronic degenerative retinal disease that leads progressive vision loss. Recent studies provide evidence that ischemia and glutamate excitotoxicity contribute to neural injury in diabetic retinopathy. This suggests that calcium release from intracellular stores is likely involved in the pathology of diabetic retinopathy.

Thus, it is evident that there is an unmet need for agents that have neuroprotective effects that can stop or retard the progressive damage to CNS neurons resulting from abnormally elevated intracellular free calcium caused by various noxious provocations.

Dantrolene, a skeletal muscle relaxant, has been found to be an antagonist of the ryanodine receptor-channel complex (See Biochemistry 2001, 40, 531-542). Dantrolene blocks calcium release from ryanodine channels when it binds to the receptor.

Dantrolene is 1-[[5-(p-Nitrophenyl)furfurylidene]amino]hydantoin.

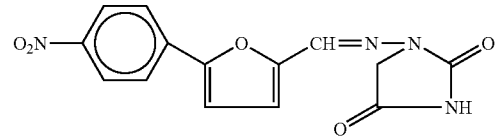

SUMMARY OF THE INVENTION

A new method of protecting the neurons in the retina and other parts of the brain of a mammal from noxious provocations has been discovered. The present method uses a ryanodine receptor antagonist to prevent or ameliorate damage to CNS neurons caused by noxious provocations that induce excessive calcium release from intracellular stores via ryanodine receptor channels. These noxious provocations, including excitotoxicity, ischemia, hypoxia, mitochondrial dysfunction, and oxidative injury, are associated with acute and chronic neural disorders, including glaucoma, diabetic retinopathy, age-related macular degeneration (ARMD), stroke, acute brain trauma, Alzheimer's disease, Parkinson's disease, and Huntington's disease. The method comprises administering to the mammal either systemically, topically, epidurally or by intrabulbar injection an effective amount of one or more ryanodine receptor antagonists, such as dantrolene (see below for details).

For protection of retinal neurons in humans suffering from glaucoma, diabetic retinopathy, and age-related macular degeneration, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include physiological saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 10% (weight by volume) and more preferably approximately 0.005% to approximately 0.5% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table 1. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 1 |
| Preservative | 0-0.10 |
| Vehicle | 0-0 |
| Tonicity Adjustor | 1-10 |
| Buffer | 0.01-10 |
| PH Adjustor | q.s pH 4.5-7.5 |
| Antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH in these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to obtain the desired concentration intravitreally that affords neuroprotection. For acute neuroprotective effect such as photoprotection in laser treatment for ARMD, the protective agent would be administered in advance of the treatment to provide optimal protection during the laser procedure. For chronic treatments such as in protection of the retinal ganglion cells against damage from the neuropathic effects of, for example, glaucoma or dry ARMD, the drug would be administered as frequently as necessary to maintain desired intravitreal concentration or range of concentrations at all times. In other words, the ophthalmic solution (or other formulation) which contains the ryanodine antagonist as the active ingredient, is administered to the mammalian eye as often as necessary to maintain the beneficial neuroprotective effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

This new method is particularly effective when administered as a prophylactic treatment, i.e. before damage to the nerve has taken place, or before long-term progression of the disease state, such as glaucoma, diabetic retinopathy, or ARMD, has taken place. Without wishing to be held to a particular theory regarding the role that the compounds of the present invention play in neuroprotection, applicants hypothesize that the compounds and methods described inhibit the intracellular $Ca+2$ release. (See for example U.S. Pat. No. 5,891,911.)

Thus it is further contemplated that the compounds of the present invention can advantageously be used in combination with compounds that inhibit cell death. Such cell death inhibiting compounds include NMDA antagonists especially memantine.

DETAILED DESCRIPTION OF THE INVENTION

The present invention is related to methods of using ryanodine receptor antagonists to protect CNS neurons, particularly the retinal neurons, from injuries caused by acute and chronic noxious provocations. The drawing will first be briefly described.

DRAWINGS

FIG. 1 is a bar graph showing the neuroprotective effect of dantrolene on NMDA-induced injury of retinal ganglion cells in vivo in rabbits. Intravitreal injection of NMDA caused retinal ganglion cell loss in control animals. Application of dantrolene ameliorated NMDA-induced damage to ganglion cells.

As mentioned above, excessive release of calcium from intracellular stores under disease conditions is cytotoxic to neurons. NMDA receptor mediated excitotoxicity is believed to be a common cause that can trigger excessive calcium release from intracellular stores in acute and chronic disorders mentioned above. For example, NMDA receptor antagonist memantine protects RGCs in glaucomatous monkeys, suggesting that the NMDA receptor mediates, at least in part, glutamate excitotoxicity in glaucoma.

There is strong evidence that damage to CNS neurons often has two stages: Primary and secondary degeneration. Initially, direct neuronal insults, such as local ischemia, trauma etc., lead to degeneration of the affected neurons. However, the associated pathophysiological and biochemical events occurring in the injured neurons are probably responsible for the subsequent progressive (secondary) degeneration of the neighboring neurons that are not directly affected by the primary insults. These secondary effects largely determine the long-term functional outcome.

The immediate injury-induced response strongly influences the subsequent degenerative response. Treatment that reduces or attenuates the injury to the primary insults is therefore likely to generate optimal results by preventing or delaying the secondary degenerative processes.

It has now been discovered that neuroprotection is conferred upon retinal neurons by administration of a ryanodine antagonist, e.g. dantrolene, to the retina of a mammal within a period prior to, or following an primary insult to the retinal neurons but prior to cell death, The terms noxious actions or noxious provocations are defined as an occurrence which is harmful or destructive to a nerve cell. It is not limited to events extrinsic to the mammal being treated but includes disease states and pathological occurrences or events, such as, for example, stroke or heart attack, that are harmful or destructive to the nerve cell via a chain of events. Non-limiting examples of noxious actions include: compressive or mechanical effects or trauma or stress factors, such as glutamate neurotoxicity, impaired blood flow to the nerves (ischemia) and with respect to the retina, glaucoma, diabetic retinopathy, retinitis pigmentosa and age-related macular degeneration.

Human Dosage and Administration

The methods of this invention are useful in treating any mammal, including humans.

According to this invention, mammals are treated with pharmaceutically effective amount of a neuroprotective agent for a period of time and at a time such that noxious provocations do not kill or permanently damage the nerve cells. Protective agents may be administered orally, topically to the eye or by any other appropriate means of delivery described below or known in the art.

In accordance with this invention, pharmaceutically effective amounts of a protective agent can be administered alone to treat neural injury or to prevent nerve cell death. Alternatively a protective agent may be administered sequentially or concurrently with another drug. For example, it may be used with an antiglaucoma drug, such as a beta-blocker, an alpha2 agonist, a muscarinic agent such as pilocarpine, a carbonic anhydrase inhibitor (CAI), or other intraocular pressure (IOP) lowering drugs. It may also be used with an anti-angiogenesis drug for the treatment of ARMD and diabetic retinopathy. The most effective mode of administration and dosage regimen of protective agent will depend on the type of disease to be treated, the severity and course of that disease, previous therapy, the patient's health status, and response to the drug and the judgment of the treating physician. Generally, the neuroprotective agent should be administered in a dose to achieve a serum or intravitreal concentration of 0.01 nM to 5 μM. Preferably the neuroprotective agent is administered prior to injury to the nerve, but can be administered after injury has occurred with lessened effect.

Conventional modes of administration and standard dosage regimens of neuroprotective agents can be used. Optimal dosages for co-administration of a drug, e.g. an IOP-lowering drug, with a neuroprotective agent can be determined using methods known in the art. Dosages of neuroprotective agents may be adjusted to the individual patient based on the dosage of the drug with which the agent is coadministered and the response of the patient to the treatment regimen. The neuroprotective agent may be administered to the patient at one time or over a series of treatments.

The agent may be administered locally, e.g. intravitreally by intrabulbar injection for ocular neuroprotection, or by intrathecal or epidural administration for spinal protection. Many of the agents of the invention can be administered systemically, e.g., orally, or intravenously, or by intramuscular injection. Additionally, agents for protection of the retina and optic nerve that are capable of passing through the cornea, and achieving sufficient concentration in the vitreous humor, may also be administered topically to the eye.

The composition used in these therapies may also be in a variety of forms. These include, for example, solid, semi-solid, and liquid dosage forms, such as tablets, pills, powders, preserved or non-preserved liquid solution or suspension, liposomes, suppositories, injectable and infusible solutions. The compositions also preferably include conventional pharmaceutically acceptable carriers which are known to those of skill in the art.

The following non-limiting examples describe assays and measurements used in 1) evaluating efficacy of neuroprotecting agents and 2) selecting ryanodine antagonists other than dantrolene.

Example 1

Experimental Procedure for Measuring Neural Protection in Rabbit Model

To evaluate in vivo neuroprotective effects of dantrolene (DTL) on NMDA-induced injury of RGCs an imaging method to count cell numbers at the RGC layer in the isolated retinas was developed. Briefly, two weeks following intravitreal injection of vehicle or various test agents, a rabbit was euthanized and the treated eye was enucleated. A piece of retina (8 mm in diameter) was cut immediately below the optic nerve head, flat-mounted in a plastic chamber filled with HEPES-buffered Ames medium, and imaged at 25 fields in a 5×5 array with a 40× water immersion objective using an Olympus microscope (BX50WI) equipped with an epi-fluorescence unit. The images were taken with a Hamamatsu C4742-95 digital camera and Image-Pro Plus software (V4.5). The total number of neurons at the ganglion cell layer in these 25 fields was counted. The same measurements were conducted in one control group (rabbits treated with vehicle) and 4 test groups treated with 1) NMDA, 2) dantrolene+NMDA, 3) veratridine (Verat) a neurotoxin that damages retinal ganglion cells with intracellular sodium overload, and 4) dantrolene+veratridine. The results from the 4 test groups are normalized with respect to that of control.

The results are reported in FIG. 1. NMDA caused a loss of 53% of cells at the RGC layer. Pretreatment with dantrolene significantly reduced NMDA-induced cell death to 35%. Dantrolene also reduced cell loss caused by veratridine from 56% to 50%.

Example 2

Assay for Selecting Ryanodine Antagonists Other Than Dantrolene

Assays for determining ryanodine antagonist may be conducted following procedures modified from that described by Laver et al., (J. Physiol. 537:763-778, 2001). Briefly, purified ryanodine receptor-channel complexes are incorporated into planar phospholipid bilayers with resting calcium gradient similar to that in a normal neuron at rest (100 nM cytoplasmic and 1 mM luminal). The level of channel activation can be determined in the presence of various ligands that activate ryanodine receptors. Effective antagonistic action of the compounds to be selected can be determined by a reduction of agonist-induced activation of the channel. The specificity of the antagonists can be determined by commercially available standard screens, such as NovaScreens.

While this invention has been described with respect to various specific examples and embodiments, it is to be understood that the invention is not limited thereby and should only be construed by interpretation of the scope of the appended claims.

What is claimed is:

1. A method of providing neural protection in a human patient suffering from age-related macular degeneration, the method comprising administering dantrolene to said patient.

2. The method of claim 1 wherein the dantrolene is administered orally or by intraocular injection.

3. The method of claim 1 wherein the dantrolene is in the form of an aqueous solution, a suspension, a gel, or a jelly.

4. The method of claim 1 wherein said age-related macular degeneration is dry age-related macular degeneration.

5. A method of providing neural protection in a human patient suffering from age-related macular degeneration, the method comprising the intravitreal injection of dantrolene to said patient.

6. A method of providing neural protection in a human patient suffering from age-related macular degeneration, the method comprising the topical administration to the eye in an ophthalmic solution of dantrolene to said patient.

* * * * *